(12) United States Patent
Chen

(10) Patent No.: US 9,629,751 B2
(45) Date of Patent: Apr. 25, 2017

(54) FIXED STRUCTURE FOR THE CONSTRICTING BAND OF SNOW GOGGLES

(71) Applicant: Chun-Nan Chen, Tainan (TW)

(72) Inventor: Chun-Nan Chen, Tainan (TW)

( * ) Notice: Subject to any disclaimer, the term of this patent is extended or adjusted under 35 U.S.C. 154(b) by 0 days.

(21) Appl. No.: 14/852,891

(22) Filed: Sep. 14, 2015

(65) Prior Publication Data

US 2017/0035614 A1    Feb. 9, 2017

(30) Foreign Application Priority Data

Aug. 7, 2015   (TW) .............................. 104212784 U

(51) Int. Cl.
*A61F 9/02*    (2006.01)

(52) U.S. Cl.
CPC .................................... *A61F 9/027* (2013.01)

(58) Field of Classification Search
CPC ........... A61F 9/02; A61F 9/027; A63B 33/002
USPC .................................... 2/439, 452, 448, 450
See application file for complete search history.

(56) References Cited

U.S. PATENT DOCUMENTS

| | | | | |
|---|---|---|---|---|
| 5,711,035 A | * | 1/1998 | Haslbeck | A61F 9/028 2/436 |
| 5,815,235 A | * | 9/1998 | Runckel | A61F 9/027 351/86 |
| 6,047,410 A | * | 4/2000 | Dondero | A61F 9/027 2/426 |
| 6,611,965 B1 | * | 9/2003 | Lee | A61F 9/027 2/431 |
| 7,100,215 B2 | * | 9/2006 | Shiue | A61F 9/025 2/443 |
| 7,162,750 B2 | | 1/2007 | Canavan | |
| 7,322,051 B1 | | 1/2008 | Wang | |
| 8,840,243 B2 | * | 9/2014 | Anselmi | G02C 3/003 2/452 |
| 2009/0260136 A1 | * | 10/2009 | Chen | A61F 9/027 2/448 |

FOREIGN PATENT DOCUMENTS

JP    WO 0232511 A1 *  4/2002 .......... A63B 33/002

* cited by examiner

*Primary Examiner* — Tejash Patel

(57) ABSTRACT

A fixed structure for the constricting band of snow goggles includes a goggle frame, a constricting band and a fastening member combined together. The goggle frame has two sides respectively provided with an insert slot and a hooking portion; the constricting band has two sides respectively fixed with a fastening body of the fastening member, and the fastening member consists of a hooking seat and the fastening body. In assembling, the hooking seat is inserted in the insert slot of the goggle frame and clasped with the hooking portion and then, the fastening body at the two sides of the constricting band is inserted in the hooking seat and positioned therein. Thus, the fixed structure for the constricting band of snow goggles can be stably combined and impossible to fall off.

1 Claim, 3 Drawing Sheets

FIXED STRUCTURE FOR THE CONSTRICTING BAND OF SNOW GOGGLES

BACKGROUND OF THE INVENTION

1. Field of the Invention

This invention relates to a fixed structure for the constricting band of snow goggles, particularly to one able to be completely and firmly engaged with the constricting band and impossible to fall off and enabling a user to wear snow goggles with great safety.

2. Description of the Prior Art

Conventionally, combination of snow goggles with a constricting band is mostly to have the constricting band directly secured at two sides of the snow goggle frame, but this combination mode is extremely inconvenient in processing; therefore, fasteners are developed and employed for combining the engage grooves bored at two sides of the snow goggle frame. However, since the snow goggle frame is made of soft rubber; therefore, when the constricting band is pulled by external force, the engage grooves of the snow goggle frame are likely to be deformed elastically and disengaged from the engaging position of the snow goggle frame, thus inconvenient in use and in assembly.

SUMMARY OF THE INVENTION

The objective of this invention is to offer a fixed structure for the constricting band of snow goggles, able to combine the constricting band together with the snow goggles more stably and impossible to fall off.

The fixed structure for the constricting band of snow goggles in the present invention includes a goggle frame, a constricting band and a fastening member combined together. The goggle frame has two sides respectively provided with an insert slot and a hooking portion; the constricting band is secured at the two sides of the goggle frame, and the fastening member is combined between the goggle frame and the constricting band and composed of a hooking seat and a fastening body. The hooking seat has one side provided with a hook and another side formed with an insert port and an engage hole, and the fastening body has one side bored with a threading slot for the constricting band to be inserted and fixed therein and another side provided with a contact surface and a protruding insert-combine member, which has an engage elastic strip fixed thereon. In assembling, the hooking seat is first inserted in the insert slot of the goggle frame and clasped with the hooking portion and then, the fastening body combined with the constricting band is inserted in the insert port of the hooking seat to have the engage elastic strip of the fastening body engaged in the engage hole of the insert port, thus finishing stable combination of the snow goggles with the constricting band.

BRIEF DESCRIPTION OF DRAWINGS

This invention will be better understood by referring to the accompanying drawings, wherein.

DETAILED DESCRIPTION OF THE PREFERRED EMBODIMENT

Figure 1:
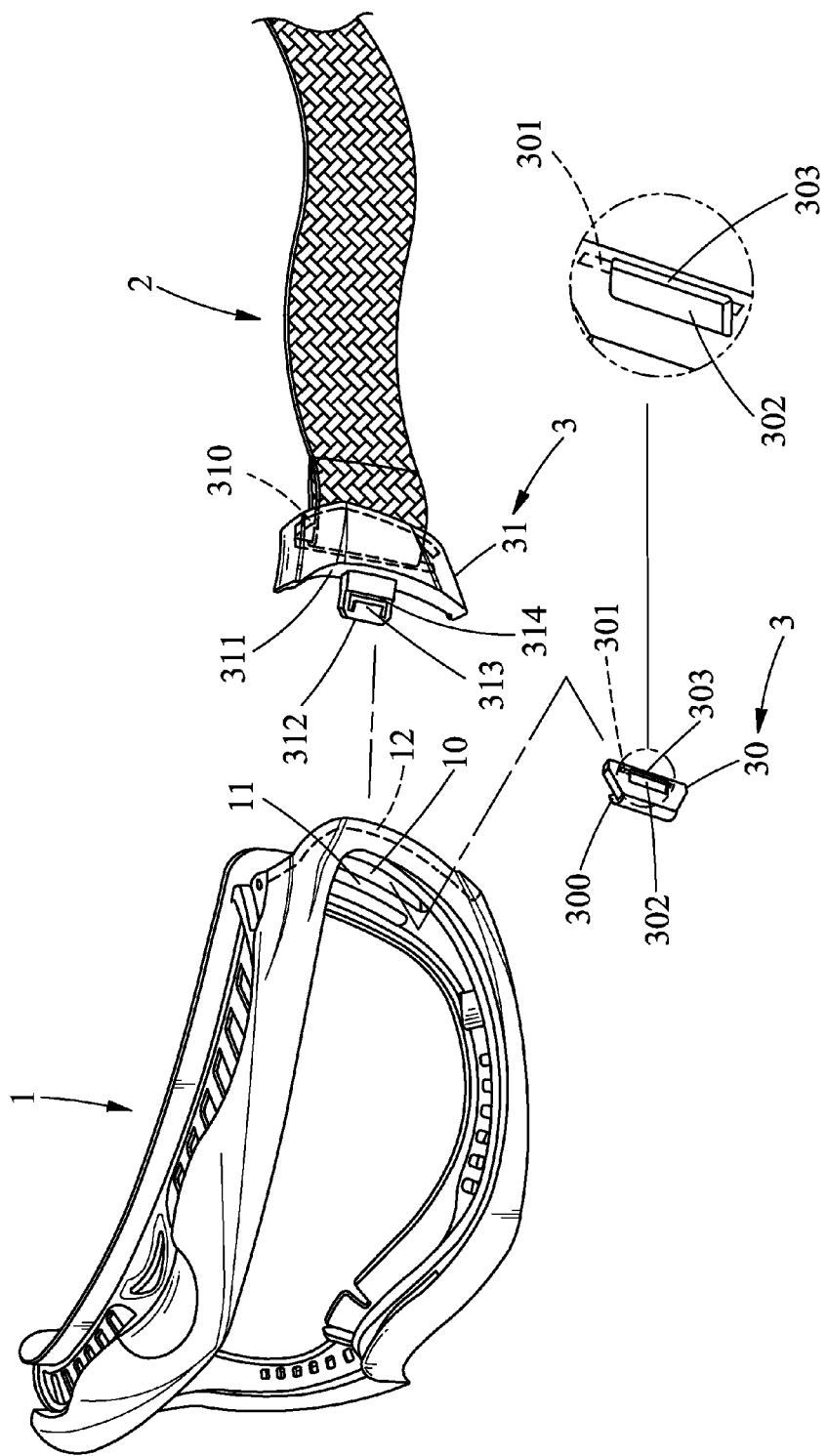
FIG. 1 is an exploded perspective view of a fixed structure for the constricting band of snow goggles in the present invention.
Figure 2:
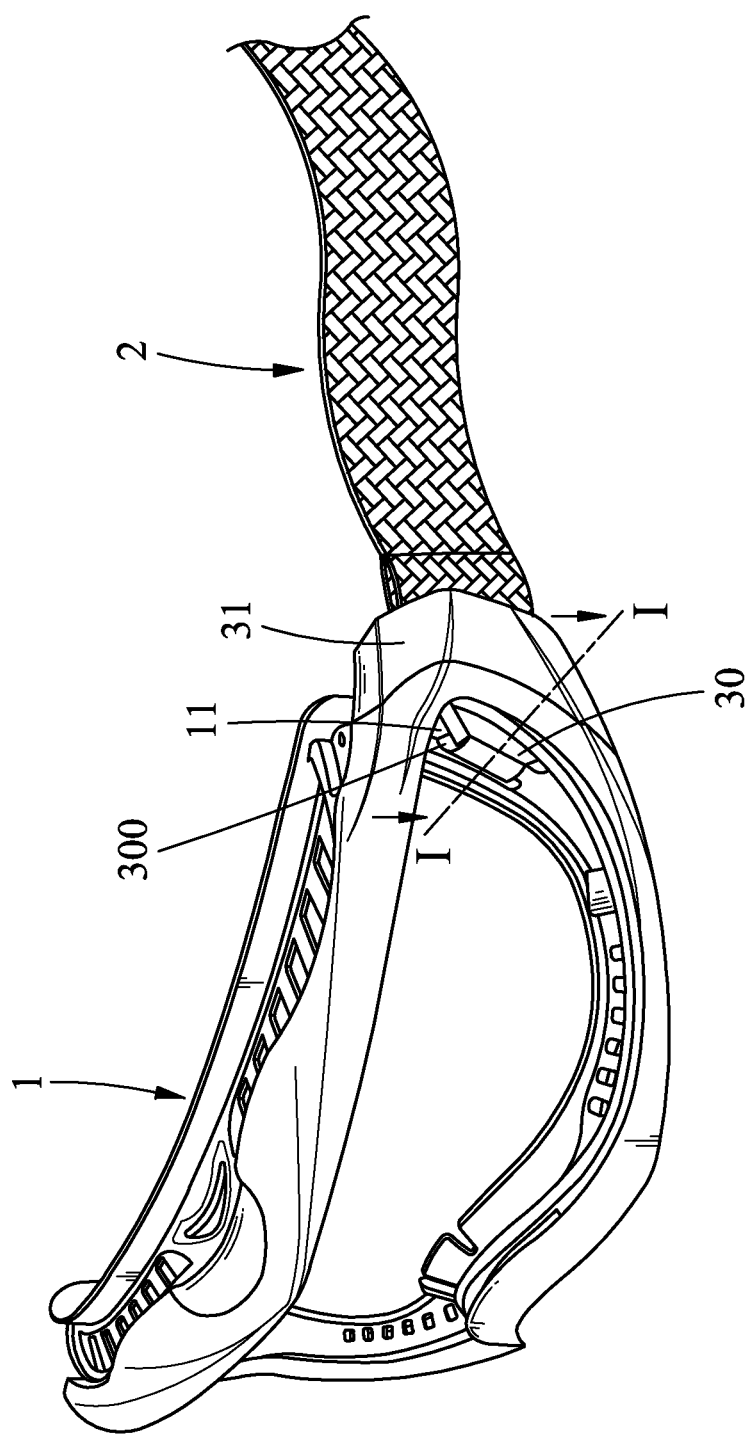
FIG. 2 is a perspective view of the snow goggles combined together with the constricting band by the fixed structure in the present invention.
Figure 3:
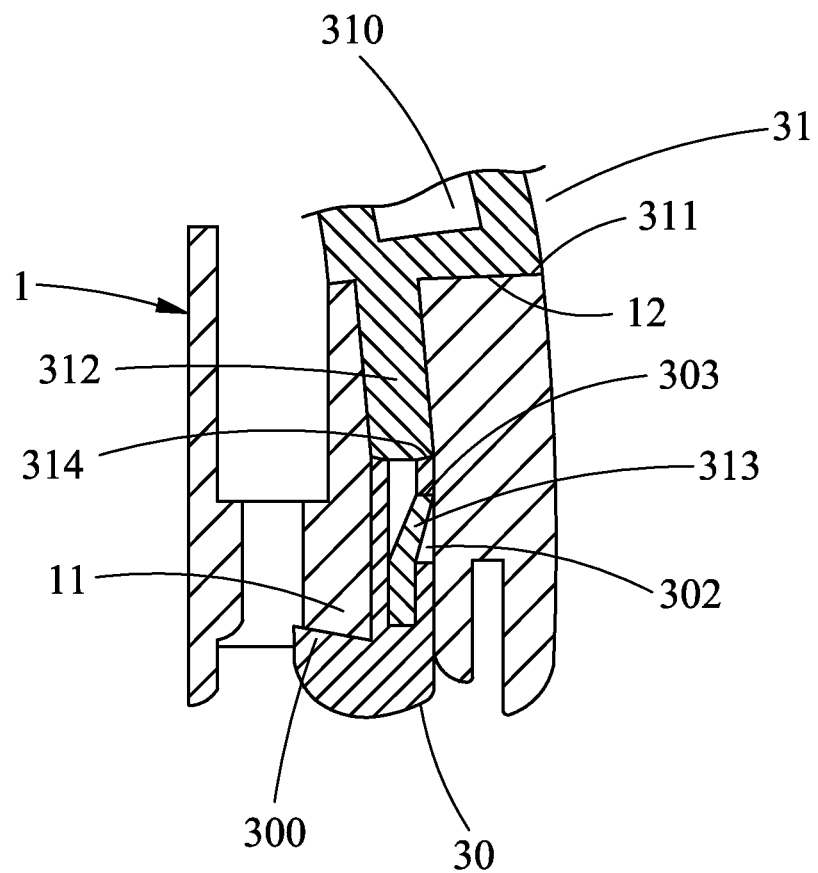
FIG. 3 is a partial cross-sectional view of a fastening state in the present invention.

A preferred embodiment of a fixed structure for the constricting band of snow goggles in the present invention, as shown in FIGS. 1-3, includes a goggle frame 1, a constricting band 2 and a fastening member 3 combined together. The goggle frame 1 made of rubber or silica gel has two end surfaces respectively provided with an insert slot 10, a hooking portion 11 and a resisting surface 12. The constricting band 2 made of elastic material is fixed at two sides of the goggle frame 1. The fastening member 3 is combined between the goggle frame 1 and the constricting band 2, composed of hooking seat 30 and a fastening body 31. The hooking seat 30 has one side formed with a protruding hook 300 and another side provided with an insert port 301, an engage hole 302 and an engage surface 303, and the hooking seat 30 is somewhat smaller than the insert slot 10 of the goggle frame 1. The fastening body 31 has one side disposed with a threading slot 310 for the constricting band 2 to be inserted therethrough and another side formed with a contact surface 311 having its central portion extending outward to form an insert-combine member 312, and an engage elastic strip 313 and a stopping surface 314 are provided at the central portion of the insert-combine member 312, the inset-combine member 312 being a little smaller than the insert port 301 of the hooking seat 30.

In using, firstly, the two ends of the constricting band 2 are respectively inserted through the threading slot 310 of the fastening body 31 and sewed and fixed in place, and the hooking seat 30 is inserted out of the insert slot 10 of the goggle frame 1 from the interior of the insert slot 10 to have the hook 300 clasped with the hooking portion 11 of the goggle frame 1. Then, the fastening body 31 fixed with the constricting band 2 is inserted in the insert port 301 of the hooking seat 30 from the two sides of the goggle frame 1. When the engage elastic strip 313 at the front end of the insert-combine member 312 of the fastening body 31 is engaged in the engage hole 302 and resists against the engage surface 303, the end surface of the insert port 301 of the hooking seat 30 will push against the stopping surface 314 of fastening body 31 and at this time, the contact surface 311 of the fastening body 31 can steadily and closely contact with the resisting surface 12 of the goggle frame 1, thus finishing combination of the snow goggles with the constricting band 2 by means of the fixed structure.

As can be known form the above description, this invention has the following characteristics and advantages:

1. This invention is to have the rigid-material fastening member 3 combined with the integrally-formed hooking portion 11 of the goggle frame 1 and have the contact surface 311 of the fastening body 31 closely attached and positioned on the resisting surface 12 of the goggle frame 1. Thus, the fastening member 3 can be completely and firmly engaged and positioned with the goggle frame 1 and impossible to slide, get loose or be separated and also impossible to fall off when pulled by external force. By so designing, the fixed structure for the constricting band of snow goggles of this invention is comparatively firm in use by having the fastening member 3 directly clasped with the hooking portion 11 of the goggle frame 1.

2. This invention can effectively solve the problem of material elastic deformation of snow goggle frame 1 and enables the snow goggles and the constricting band to be tightly combined together and impossible to fall off.

While the preferred embodiment of the invention has been described above, it will be recognized and understood that various modifications may be made therein and the appended claims are intended to cover all such modifications that may fall within the spirit and scope of the invention.

What is claimed is:

1. A fixed structure for the constricting band of snow goggles comprising:
    a goggle frame, said goggle frame having two sides respectively provided with an insert slot and a hooking portion;
    a constricting band assembled at two sides of said goggle frame; and
    a fastening member combined between said goggle frame and said constricting band, said fastening member composed of a hooking seat and a fastening body, said hooking seat having one side provided with a hook and another side formed with an insert port and an engage hole, said fastening body having one side bored with a threading slot for said constricting band to be inserted therethrough and fixed therein, said fastening body having another side formed with a contact surface and a protruding insert-combine member, said insert-combine member having an elastic strip secured thereon;
    said hooking seat inserted into said insert slot of said goggle frame and clasped with said hooking portion, the hooking seat being almost the same size as the insert slot for firmly positioning the hooking seat in the insert slot, then said fastening body, which is combined together with said constricting band, inserted in said insert port of said hooking seat to have said engage elastic strip of said fastening body engaged with said engage hole of said insert port, thus finishing stable combination of said snow goggles with said constricting band.

* * * * *